(12) United States Patent
Hart

(10) Patent No.: US 7,700,132 B2
(45) Date of Patent: *Apr. 20, 2010

(54) ISOLATED MATERIAL HAVING AN ANTI-ORGANOTROPHIC EFFECT

(75) Inventor: John Ernest Hart, Hants (GB)

(73) Assignee: Endocrine Pharmaceuticals Limited, Hampshire (GB)

( * ) Notice: Subject to any disclaimer, the term of this patent is extended or adjusted under 35 U.S.C. 154(b) by 427 days.

This patent is subject to a terminal disclaimer.

(21) Appl. No.: 11/170,959

(22) Filed: Jun. 30, 2005

(65) Prior Publication Data

US 2005/0244507 A1 Nov. 3, 2005

Related U.S. Application Data

(63) Continuation of application No. 09/856,944, filed as application No. PCT/GB99/04013 on Dec. 1, 1999, now Pat. No. 7,572,465.

(30) Foreign Application Priority Data

Dec. 1, 1998 (GB) .................................. 9826186.0

(51) Int. Cl.
*A61K 35/14* (2006.01)
*A61K 35/16* (2006.01)
*A61K 38/00* (2006.01)

(52) U.S. Cl. ........................ 424/529; 424/530; 424/531; 514/2; 514/21

(58) Field of Classification Search .................. 424/520
See application file for complete search history.

(56) References Cited

U.S. PATENT DOCUMENTS 4,734,398 A 3/1988 Di Zerega

OTHER PUBLICATIONS

Hart, J.E., "Pituitary-related weight changes affecting the liver, uterus and adrenal glands of rats treated . . . ," Toxicology (Apr. 1990), p. 185-194, vol. 61, No. 2.

*Primary Examiner*—Vera Afremova
(74) *Attorney, Agent, or Firm*—Saliwanchik, Lloyd & Saliwanchik

(57) ABSTRACT

An endogenous mammalian material has been found which has the biological effect of causing a reduction in the mass of mammalian organs including the heart and prostate. The material has physico-chemical properties such that it appears as a compound of molecular weight between 10 and 20 kD when subjected to a purification process using membrane filtration followed by gel filtration. This material has therapeutic uses including the treatment of organ or tissue hypertrophy and hyperplasia.

3 Claims, 3 Drawing Sheets

ISOLATED MATERIAL HAVING AN ANTI-ORGANOTROPHIC EFFECT

CROSS-REFERENCE TO RELATED APPLICATIONS

This application is a continuation of U.S. application Ser. No. 09/856,944, filed Jul. 16, 2001, now U.S. Pat. No. 7,572, 465, which is a National Stage Application of International Application Number PCT/GB99/04013, filed Dec. 1, 1999, which claims priority to GB9826186.0, filed Dec. 1, 1998, which are hereby incorporated by reference in their entireties, including any figures, tables, nucleic acid sequences, amino acid sequences, or drawings.

FIELD OF THE INVENTION

The present invention relates to an isolated material which generally reduces organ mass, and to its therapeutic use.

BACKGROUND OF THE INVENTION

The mammalian gonads secrete a variety of hormones, such as oestrogen and testosterone, and other signalling molecules, such as growth factors and cytokines, which have effects throughout the body. Mechanisms regulating the masses of tissues and organs can in their totality be described as the "organotrophic system". The endocrine (hormonal) contribution to this system includes the hypothalamic-pituitary-gonadal axis, the adrenals, the thyroid and other endocrine tissues. Among the generally positive endocrine influences in the organotrophic system are oestrogen and testosterone. Organotrophic effects of oestrogens are discussed by Hart, Pharmac. Ther. (1990) 47:203-218.

Hart, Toxicology (1990) 61:185-194, reported that the oestrogen antagonist, clomiphene, could decrease most organ weights in female rats. Hart postulated that clomiphene may act as an antagonist of the known positive organotrophic oestrogen effect.

SUMMARY OF THE INVENTION

The present invention is based on the discovery of an endogenous material (described herein as "micrin") which can diminish the size and weight of many organs and tissues throughout the body. Micrin can be obtained by a process which comprises:

(i) treating a female mammal with clomiphene citrate (this step is optional);

(ii) collecting ovarian venous blood from the mammal;

(iii) preparing ovarian venous plasma from the blood collected in step (ii); and (iv) at least partially purifying micrin from the ovarian venous plasma.

Micrin may be defined as an endogenous material which is inducible by clomiphene and has the effect in general of reducing organ or tissue mass in a mammalian body. Micrin may be a single compound or a group of compounds. Micrin has a molecular weight range of nominally 10-20 kD when purified from blood as defined herein although it is possible that it is a larger or smaller moiety having physico-chemical properties which cause it to behave as if it were a moiety of 10-20 kD. Further, it is possible that the active component is of lower molecular weight through its being associated (covalently, or more likely non-covalently) with a carrier, or by being a fragment of the micrin that has been identified, or that the 10-20 kD moiety is a biologically active fragment of a larger entity.

Without wishing to be bound by theoretical considerations, it is believed that micrin is a newly discovered hormone produced principally by mammalian gonads, although other sources of the hormone are contemplated. This is the first time that a hormone with widespread negative influence on organ size has been discovered. Indeed there existed a technical prejudice in the art, away from the presence invention, which believed there were mainly positive endocrine influences on organ size; organ shrinkage being presumed to be brought about by absence of a positive factor (such as for example pituitary trophic hormones). This invention introduces a novel entity (micrin) which is generally a negative influence on organ size (although individual organs may respond differently).

The mechanism of action of micrin is not yet understood. It may involve one or more of cell shrinkage, inhibition of cell division and an increased effect in apoptosis, or micrin may be associated with a substance having such effects.

DESCRIPTION OF THE INVENTION

Figure 1:
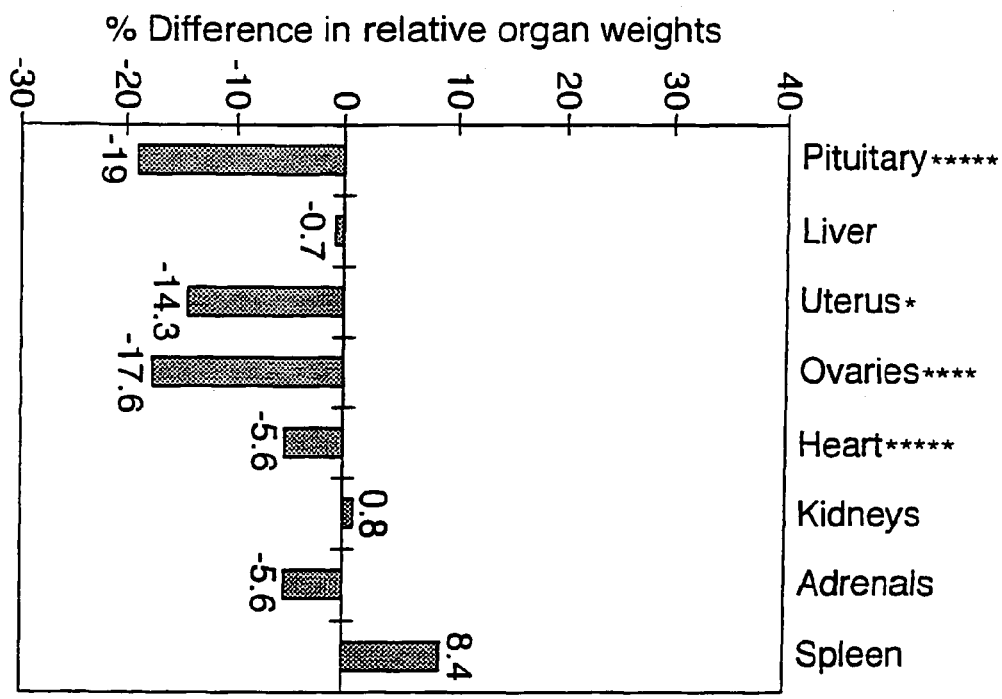
FIGS. 1 to 5 each show the results of bioassays, versus controls, of the effect of micrin, at various stages of isolation, on the weights of various organs.

With reference to the four-step process defined above, step (iv) preferably comprises obtaining the 10-30 kD molecular weight fraction from ovarian venous plasma, for example by membrane filtration. More preferably, step (iv) comprises obtaining the 10-20 kD molecular weight fraction from ovarian venous plasma, for example by gel filtration chromatography. Most preferably, step (iv) further comprises subjecting the 10-20 kD fraction to further purification by ion exchange chromatography and collecting the fraction eluted in 0.1-0.2 M NaCl. The procedure is fully described in the Examples, below. The following Protocol and Flow Diagram are summaries:

Protocol

1. Plasma cleared by centrifugation at +4° C. and 4000 rpm for 5 minutes.
2. Cleared plasma spun through Amicon Centriprep-30 cartridges at 2000 rpm to give a nominal 0-30 kD fraction.
3. Nominal 0-30 kD fraction spun through Amicon Centriprep-10 to give a nominal 10-30 kD sub-fraction.
4. Nominal 10-30 kD sub-fraction concentrated and gel filtered through a Pharmacia FPLC Superdex-75 column to give a nominal 10-20 kD sub-fraction.
5. Nominal 10-20 kD sub-fraction repeatedly concentrated and buffer diluted and applied to a Pharmacia FPLC Mono-Q ion exchange column eluted with a gradient of 0-0.3. M NaCl. Eluate divided into 0-0.1 M, 0.1-0.2 M and 0.2-0.3 M NaCl ion exchange fractions.

FLOW DIAGRAM

PLASMA

↓ Centrifuge

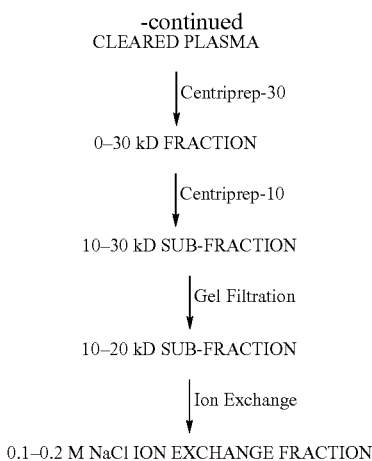

CLEARED PLASMA
↓ Centriprep-30
0–30 kD FRACTION
↓ Centriprep-10
10–30 kD SUB-FRACTION
↓ Gel Filtration
10–20 kD SUB-FRACTION
↓ Ion Exchange
0.1–0.2 M NaCl ION EXCHANGE FRACTION If necessary or desired, further, standard purification/fractionation procedures may be conducted. These include physico-chemical methods, such as HPLC, FPLC, gel filtration, electrophoresis, column chromatography, ion exchange chromatography, isoelectric focusing, or using immuno-affinity columns.

The presence of micrin at any stage can be confirmed by the bioassay reported below, as Example 3. Micrin may also exist in other fractions than those obtained by the recited steps, but its effect is generally less in such other fractions.

Micrin-rich plasma may be obtained from a suitable mammal such as a sheep. For example, the sheep (approximately 70 kg) is treated with clomiphene citrate at 1.5 g/day on Day 3 post-oestrus of its reproductive cycle and the following 3 days, as described herein. Depending on factors such as the age of the sheep, clomiphene induction may be unnecessary.

Preferably, the micrin, e.g. obtained by the given procedure, has a specific activity of at least 1 unit/ml. A unit of micrin is defined as an amount of micrin which when administered daily is sufficient to decrease the relative (post-exsanguination) organ weight of the female rat heart by 5% when administered in 4 equal daily doses using the bioassay described herein.

Micrin has therapeutic utility. In particular, it may be used for the treatment of organ or tissue hypertrophy and/or hyperplasia in a mammal. Specific conditions that may be treated include, for example, cardiac or prostatic hypertrophy, polycystic ovarian syndrome, endometriosis polycystic renal disease and pituitary adenoma.

For this purpose, it may be used in the form obtained by extraction or further purification, as described above, or it may be formulated, as a medicament. Thus, according to another aspect of the present invention, a pharmaceutical composition comprises micrin and a pharmaceutically acceptable excipient or carrier. A preferred pharmaceutical composition is suitable for parenteral administration such as, for example, an injectable solution, preferably sterile. Other suitable non-injectable methods of administration, for which micrin may be formulated as appropriate, are oral and nasal.

Suitable carriers and excipients, and other suitable additives, are known to those skilled in the art. For example, a micrin solution may be prepared in a sterile form using any suitable technique such as for example sterile filtration.

The dosage to be administered can be determined, having regard to typical factors, by one skilled in the art. A suitable dosage is 1-25 ml/day of micrin having a specific activity of about 1 unit/ml. A preferred dosage is 2.5-10 ml/day and especially 5 ml/day.

Micrin may also be used as a research tool for exploring a novel mammalian micrin hormone system and/or the organotrophic system. It may also be used to screen for agonists or antagonists of micrin such as, for example, by mixing a potential agonist or antagonist compound with the partially purified micrin described herein and measuring differences in the bioassay described herein compared with appropriate controls. Micrin may also be used as a surrogate marker in clinical trials, to screen potential drugs for undesirable toxicological properties on the micrin hormonal system as detectable in the bioassay described herein, and to detect effects on the wider organotrophic system.

Figure 2:
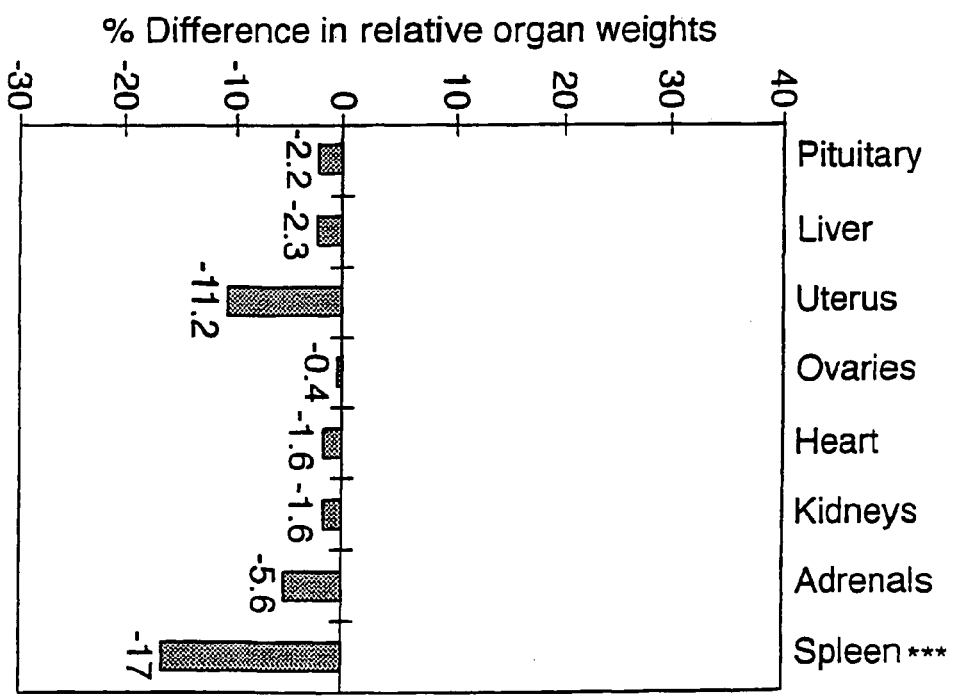
Figure 3:
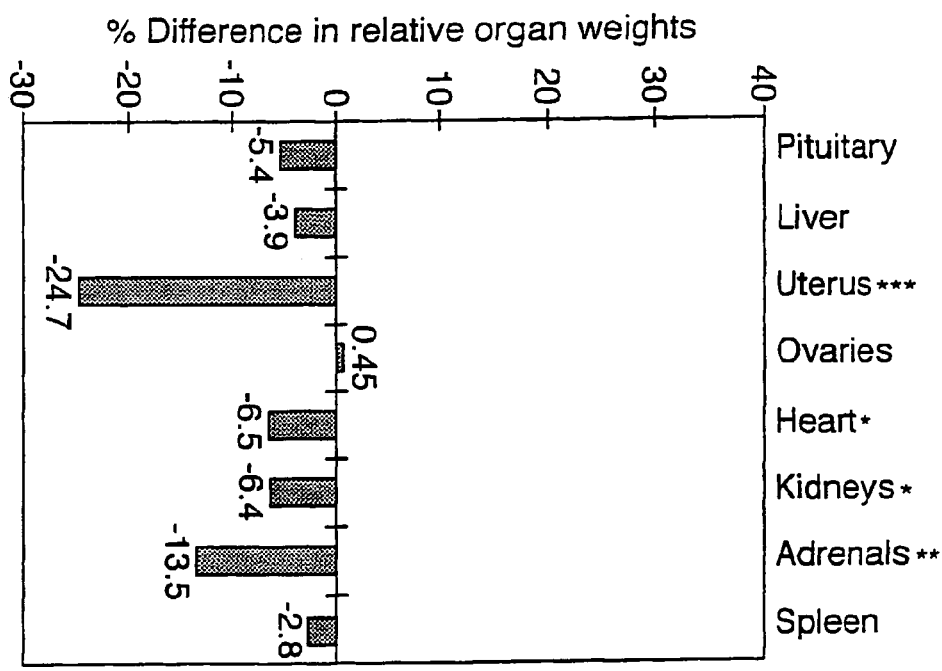
Figure 4:
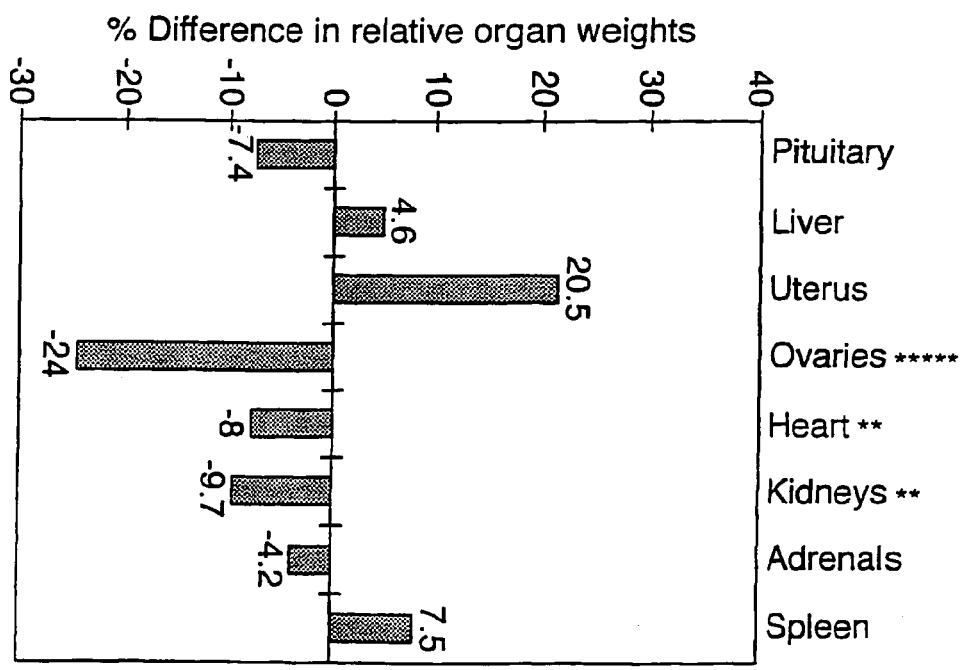
Figure 5:
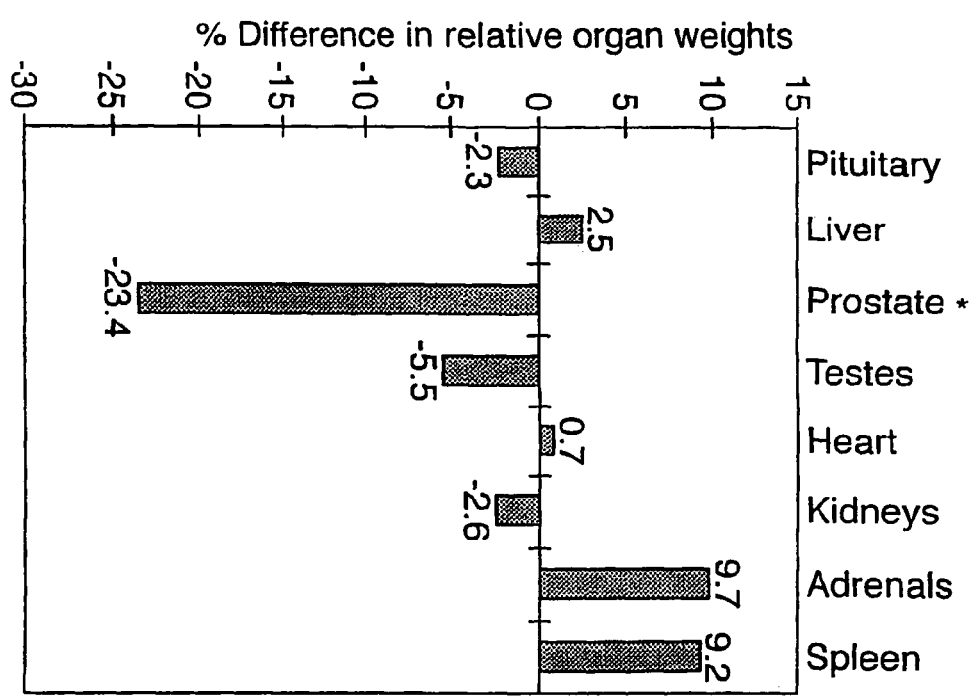

The following Examples illustrate the invention, with reference to the accompanying drawings, in which:

FIG. 1 illustrates a bioassay (n=10) of test ovarian venous plasma from a clomiphene-treated sheep ("active plasma") in the female rat versus a control of jugular venous plasma from an ovariectomised ("ovx") sheep, untreated with clomiphene;

FIG. 2 illustrates the bioassay (n=11) of a 10-30 kD fraction of active plasma in the female rat versus a control of a 10-30 kD fraction of ovx sheep venous plasma;

FIG. 3 illustrates the bioassay (n=8) of a 10-20 kD sub-fraction of active plasma in the female rat versus a control (n=5) of a 10-20 kD sub-fraction of ovx sheep venous plasma;

FIG. 4 illustrates the bioassay (n=5) of a 0.1-0.2 M NaCl ion exchange fraction ("active ion exchange fraction") of the 10-20 kD sub-fraction of active plasma in the female rat versus a control (n=20) of physiological, pyrogen-free saline; and FIG. 5 illustrates the bioassay (n=5) of the active ion exchange fraction in the male rat versus a control of a 0.1-0.2 M NaCl ion exchange fraction of the 10-20 kD sub-fraction of ovx sheep venous plasma.

The data in the Figures were obtained thus: the mean relative (post-exsanguination) organ weights of the test rats were first expressed as a percentage of the control means. These figures were then subtracted from 100 to yield the percentage difference between test and control means, the results being plotted against a zero baseline representing control values. The asterisks in the Figures represent the statistical significance, thus:

$* = p < 0.05,  = p < 0.02, * = p < 0.01,$ $** = p < 0.002, *** = p < 0.001.$

The statistical analysis involved Student's t-test.

Example 1

Preparation of Micrin

1. Isolation of Sheep Ovarian Venous Plasma

Multiparous non-pregnant ewes were used. Ewes were housed with a vasectomised ram to detect the day of oestrus (day 0). On day 3, post-oestrus ewes were injected intramuscularly with clomiphene citrate (Sigma Chemical Co., Poole, UK, catalogue no. C6272) at a dose of 1.5 g/day, dissolved in warm physiological, pyrogen-free saline to a final volume of 10 ml. Clomiphene injections were repeated on days 4, 5 and 6 post-oestrus. On day 6, post-oestrus and under pentobarbitone (RMB Animal Health Ltd., Dagenham, UK) anaesthesia, ovarian venous blood was collected from the sheep, following the method of Heap et al, J. Reprod. Fert. (1985) 74:645-656, into heparin (1 i.u./ml blood) (C.P. Pharmaceuticals Ltd., Wrexham, UK) to prevent clotting. Blood samples were immediately placed on ice until centrifugation. The ovarian venous plasma was then obtained from the ovarian venous blood by centrifugation at +4° C. and 4000 rpm for 20 minutes. The plasma layer was then removed and stored in a plastic bottle in a freezer at –10° C.

2. Preparation of the Nominal 0-30 kD Molecular Weight Fraction from Sheep Ovarian Plasma The plasma (from 1 above) was cleared by centrifugation at +4° C. and 4000 rpm for 5 minutes. The cleared plasma fraction was then poured into an Amicon Centriprep-30, a centrifuge device with concentric inner and outer compartments separated by a membrane having a nominal cut off size of 30 kD. The device was spun at 2000 rpm for 2 hours at +4° C. The filtrate that had collected in the inner compartment was removed by pipetting and the centrifugation continued for a further 2 hours. This procedure was repeated a further two times after which the inner compartment with the membrane was replaced. The series of centrifugations was then repeated. By this means, 20 ml of filtrate, the nominal 0-30 kD fraction, was obtained from the plasma fraction. The nominal 0-30 kD fraction was stored in a plastic bottle at –10° C. or used in 3 below.

3. Preparation of the Nominal 10-30 kD Molecular Weight Sub-Fraction from Sheep Ovarian Plasma The nominal 0-30 kD plasma fraction, from 2 above, was poured into an Amicon Centriprep-10, having a nominal cut off size of 10 kD. The device was spun at 2000 rpm for one hour at +4° C. The filtrate that had collected in the inner compartment was removed by pipetting and the procedure was repeated until approximately 2 ml of sample remained in the outer compartment. This was diluted to 15 ml with phosphate-buffered saline (PBS) and the centrifugation repeated until the volume in the outer compartment was reduced to approximately 2 ml. The resultant fraction, the nominal 10-30 kD sub-fraction, was stored in a plastic bottle at –10° C. or used in 4 below.

4. Preparation of the Nominal 10-20 kD Molecular Weight Sub-Fraction from Sheep Ovarian Plasma The nominal 10-30 kD plasma sub-fraction, from 3 above, was then concentrated to 800 µl with an Amicon Centricon-10, a small centrifuge device fitted with a membrane having a nominal cut off of 10 kD, by spinning in a centrifuge at 2000 rpm for one hour. 200 µl aliquots were then applied to an FPLC gel filtration column (Pharmacia Superdex-75, HR 10/30, 30 cm long, 1 cm diameter) that had been calibrated with protein molecular weight standard. Elution was carried out with 25 ml PBS over a period of 25 minutes and 0.5 ml fractions were collected. Fractions falling within the nominal 10-20 kD molecular weight range were pooled, to give the nominal 10-20 kD sub-fraction, and stored in a plastic bottle at –10° C. or used in 5 below.

5. Preparation of the Three Ion-Exchange (Sodium Chloride) Fractions from the Nominal 10-20 kD Sub-Fraction of Sheep Ovarian Plasma The nominal 10-20 kD molecular weight sub-fraction of sheep ovarian plasma, from 4 above, was concentrated by centrifugation in an Amicon Centricon-3 (5 ml down to 1 ml). The concentrated fraction was subjected to buffer exchange with 20 mM Tris.HCl buffer, pH 7, by repeated dilution and reconcentration in an Amicon Centriprep-3 and Centricon-3. 500 µl aliquots were then applied to a FPLC ion exchange column (Pharmacia Mono-Q, HR 5/5, 4 cm long, 0.5 cm diameter) and eluted with a linear gradient of 0-0.3 M sodium chloride solution in 20 mM Tris.HCl buffer, pH 7. The elution ran for 15 minutes at a flow rate of 1 ml/minute and 0.5 ml fractions were collected. The eluate fractions were divided into three pools corresponding to 0-0.1 M, 0.1-0.2 M and 0.2-0.3 M sections of the NaCl gradient Example 1A In order to improve yields, certain procedures recited in Example 1 may be changed, as follows:

2. Preparation of the Nominal 0-30 kD Molecular Weight Fraction from Sheep Ovarian Plasma The plasma was cleared by centrifugation at 2000 g, or equivalent for 10 minutes. The cleared plasma (120 ml) was then dispensed into 8× Amicon Centriprep-30 filtration units and centrifuged at 1800 rpm for 10-12 hours at +4° C. The filtrate was harvested at intervals and centrifugation continued until a final volume of 80 ml was obtained. This nominal 0-30 kD fraction was stored overnight in polypropylene tubes at –20° C.

3. Preparation of the Nominal 3-30 kD Molecular Weight Fraction from Sheep Ovarian Plasma The nominal 0-30 kD molecular weight fraction (generated as detailed in 2. above) was dispensed into 6× Amicon Centriprep-3 filtration units and centrifuged at 1800 rpm for 8-10 hours at +4° C. Centrifugation was performed until 2 ml of retentate remained in the outer compartment of each Centriprep-3 unit. The retentate (3-30 kD molecular weight sub fraction) was stored overnight at –20° C. The retentate was subsequently, concentrated to a final volume of 500 µl in an Amicon Centricon-3 unit. After centrifuging the samples at 3000 rpm for 1-2 hours at +4° C., the retentate was placed on ice before applying to the gel filtration column as detailed in 4. below.

4. Preparation of the Nominal 10-20 kD Molecular Weight Sub Fraction from Sheep Ovarian Plasma Samples (2×200 µl) prepared in 3. above were subsequently applied to an FPLC gel filtration column (Pharmacia Superdex-75, HR 10/30, 30 cm long, 1 cm diameter) that had been calibrated with protein molecular weight standards. Elution was effected in PBS and fractions (1 ml/tube) were collected over a period of 45 minutes. Fractions falling within the nominal 10-20 kD molecular weight range were pooled and concentrated to 2 ml by centrifugation in a Centriprep-3 unit (1800 rpm for 1-2 hours at +4° C.). The retentate was either stored in polypropylene tubes at –20° C. or used in 5. below.

5. Preparation of Ion Exchange (Sodium Chloride) Fractions from the Nominal 10-20 kD Molecular Weight Sub Fraction of Sheep Ovarian Plasma The concentrated fraction generated in 4. above was subjected to buffer exchange by dilution to 15 ml in 20 mM Tris.HCl buffer, pH 7.6. The Centriprep-3 unit was centrifuged as before for (1800 rpm at +4° C.) 6-8 hours. This fraction was further concentrated to ~500 µl in Centricon-3 units (3000 rpm for 1-2 hours at +4° C.). Samples (2×200 µl) were then applied to a Vydac's Protein SAX HPLC ion exchange column (0.75×5 cm) and eluted with a linear gradient of 0-1 M sodium chloride in 20 mM Tris.HCl buffer, pH 7.6. Eluted fractions (2 ml/tube) were collected over 45 minutes and activity tested in the rat bioassay (Example 3).

Example 2

Pharmaceutical Composition

Sterile-filtered micrin (5.5 ml; specific activity 1 unit/ml, as described herein) as the 0.1-0.2 M NaCl active ion exchange fraction as described herein and suitably diluted with physiological, pyrogen-free saline, and supplied in a sterile glass vial. The dose (5 ml) can be administered by injection into the peritoneum using a sterile needle.

Example 3

Bioassay

Whole plasma and the various fractions of partially purified micrin from Example 1 above were tested by in vivo bioassay as described below:

Adult female Wistar albino rats (weight 200-220 g) or adult male Wistar albino rats (weight 300-400 g) were injected intraperitoneally using sterile needles, 0.5×16 mm, 25 g, with daily 1×1 ml doses of the sheep ovarian venous plasma (or one of the other fractions prepared in Example 1 above) for four days. Ninety-six hours after the commencement of dosing, the rats were then anaesthetised (terminally using carbon dioxide) and the thorax opened surgically. The rats were then partially exsanguinated by cardiac puncture (5 ml); and then each of the rats underwent whole body dissection as described by Hart, Toxicology (1990) 61:185-194.

The following organs were removed from the partially exsanguinated female rats in a standard order, trimmed free of connective tissue and fat, and weighed: heart, liver, pituitary gland, adrenal glands, kidneys, spleen, uterus and ovaries; from male rats: heart, liver, pituitary gland, adrenal glands, kidneys, spleen, prostate and testes. Each of the organs was weighed and the results expressed as a percentage of the whole rat terminal body weight (g/kg or %).

Control experiments were carried out using the same procedure with sheep jugular whole venous plasma and similar fractions (molecular weight or ion exchange fractions) derived from sheep jugular venous plasma obtained as above in Example 1, but from ovariectomised sheep, clomiphene-untreated.

The results of reduction in organ mass obtained using the active plasma, fractions of active plasma, sub-fractions of active plasma and ion exchange fractions of active plasma are given in FIGS. 1 to 5.

The invention claimed is:

1. A purified material, inducible in a mammal post-oestrus by clomiphene, and having the ability to reduce the mass of body organs including non-gonadal organs, of a live adult mammal, wherein said material is present in a nominal 10-30 kD sub-fraction of ovarian venous plasma prepared from ovarian venous blood collected from a mammal post-oestrus;

and wherein said material has a specific activity of at least 1 unit/ml, wherein a unit is defined as an amount of the material which, when administered daily, is sufficient to decrease the relative (post-exsanguination) organ weight of a female rat heart by at least 5% when administered in 4 equal daily doses.

2. The material according to claim 1, wherein the mammal is a sheep.

3. A pharmaceutical composition comprising the material of claim 1 and a pharmaceutically acceptable carrier.

\* \* \* \* \*